US008666023B2

(12) United States Patent
Omura

(10) Patent No.: US 8,666,023 B2
(45) Date of Patent: Mar. 4, 2014

(54) RADIATION IMAGING APPARATUS

(75) Inventor: Satoru Omura, Chigasaki (JP)

(73) Assignee: Canon Kabushiki Kaisha, Tokyo (JP)

( * ) Notice: Subject to any disclaimer, the term of this patent is extended or adjusted under 35 U.S.C. 154(b) by 320 days.

(21) Appl. No.: 12/970,679

(22) Filed: Dec. 16, 2010

(65) Prior Publication Data
US 2011/0150182 A1 Jun. 23, 2011

(30) Foreign Application Priority Data

Dec. 21, 2009 (JP) ................... 2009-288829

(51) Int. Cl.
H05G 1/58 (2006.01)
H05G 1/64 (2006.01)

(52) U.S. Cl.
USPC .......................... 378/98.5; 378/116

(58) Field of Classification Search
USPC ................. 378/98.5, 115, 116, 117
See application file for complete search history.

(56) References Cited

U.S. PATENT DOCUMENTS

| 6,859,513 B2* | 2/2005 | Sako ................. 378/16 |
| 2007/0165783 A1* | 7/2007 | Abu Tabanjeh ................ 378/116 |
| 2007/0253534 A1* | 11/2007 | Abe ................. 378/116 |
| 2009/0086915 A1* | 4/2009 | Takenaka et al. ............. 378/116 |
| 2009/0232278 A1* | 9/2009 | Ohara ............... 378/116 |

FOREIGN PATENT DOCUMENTS

| JP | 2009-045150 A | 3/2009 |
| WO | 2009031411 A1 | 3/2009 |

* cited by examiner

Primary Examiner — Irakli Kiknadze
(74) Attorney, Agent, or Firm — Canon USA Inc. IP Division

(57) ABSTRACT

A radiation imaging apparatus communicating with a radiation imaging control apparatus for controlling an operation of acquiring a radiation image includes a radiation detection unit configured to detect radiation and to acquire the radiation image, a storage unit configured to store information about a plurality of the radiation imaging control apparatuses, a selection unit configured to select one of the plurality of the radiation imaging control apparatuses as an apparatus to communicate with the radiation imaging apparatus, and a setting unit configured to set communication with the radiation imaging control apparatus selected by the selection unit.

18 Claims, 8 Drawing Sheets

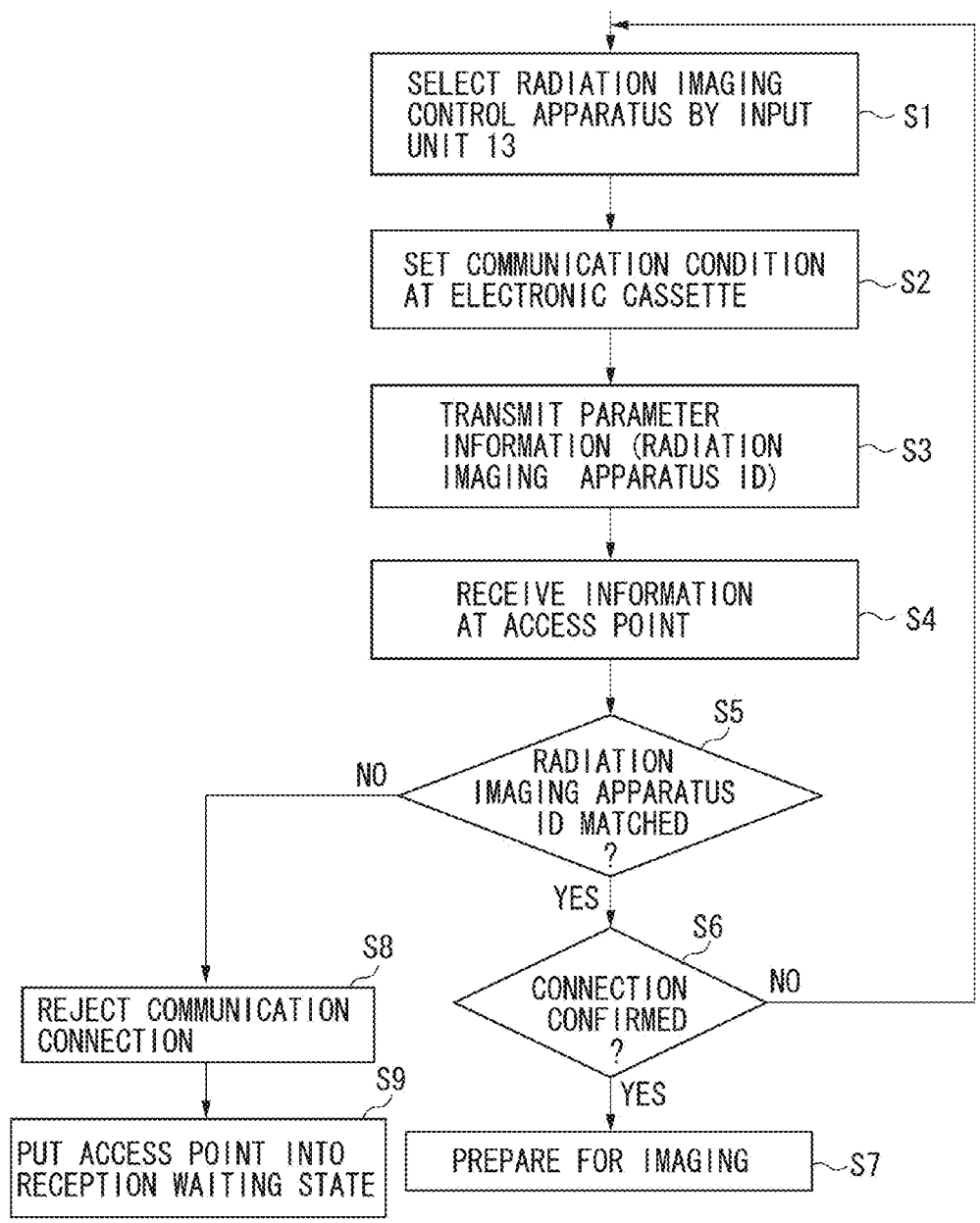

RADIATION IMAGING APPARATUS

BACKGROUND OF THE INVENTION

1. Field of the Invention

The present invention relates to a radiation imaging apparatus for detecting radiation and acquiring a radiation image.

2. Description of the Related Art

In a conventional digital radiation imaging system using digital radiography (DR), a radiation imaging apparatus (electronic cassette) has cables for supplying electric power and transmitting and receiving images and control signals to and from an imaging control apparatus.

However, with spread of portable electronic cassettes, in consideration of ease of handling of cassettes and breakage in the cable that may cause hindrance to imaging, a cableless electronic cassette has been commercialized, which can wirelessly communicate with an imaging control apparatus. The wireless communication type electronic cassettes can improve handlability. However, if there is a plurality of such electronic cassettes, because the electronic cassettes are of the cableless type, a state of communication between an imaging control unit and each electronic cassette is difficult to grasp.

Japanese Patent Application Laid-Open No. 2009-45150 discusses a digital radiation imaging system which includes a plurality of electronic cassettes and can select a desired electronic cassette from among the plurality of electronic cassettes to perform communication by operating an imaging control apparatus.

Generally, when radiation imaging is performed, an electronic cassette is arranged in a radiation imaging room, and a radiation imaging control apparatus is arranged in a separate room. At that time, first, the electronic cassette is located on a test object. Then, the radiation imaging control apparatus in the separate room is operated. Thus, if there is a plurality of electronic cassettes in the radiation imaging room, when an electronic cassette is located on the test object, mix-up of the electronic cassette can occur.

In the digital radiation imaging system discussed in Japanese Patent Application Laid-Open No. 2009-45150, the radiation imaging control apparatus in the separate room can confirm which of electronic cassettes is communicating therewith. However, in the radiation imaging room, an operator cannot confirm which electronic cassette is communicating with the radiation imaging system. Accordingly, the operator needs to go to the separate room.

SUMMARY OF THE INVENTION

The present invention has been accomplished in consideration of the above situation and is directed to improvement of operability of a wireless communication type radiation imaging apparatus.

According to an aspect of the present invention, a radiation imaging apparatus communicating with a radiation imaging control apparatus for controlling an operation of acquiring a radiation image includes a radiation detection unit configured to detect radiation and to acquire the radiation image, a storage unit configured to store information about a plurality of the radiation imaging control apparatuses, a selection unit configured to select one of the plurality of the radiation imaging control apparatuses as an apparatus to communicate with the radiation imaging apparatus, and a setting unit configured to set communication with the radiation imaging control apparatus selected by the selection unit.

Further features and aspects of the present invention will become apparent from the following detailed description of exemplary embodiments with reference to the attached drawings.

BRIEF DESCRIPTION OF THE DRAWINGS

The accompanying drawings, which are incorporated in and constitute a part of the specification, illustrate exemplary embodiments, features, and aspects of the invention and, together with the description, serve to explain the principles of the invention.

FIGS. 3A and 3B are flowcharts illustrating a process performed by the system according to the first exemplary embodiment of the present invention.

DETAILED DESCRIPTION OF THE EMBODIMENTS

Various exemplary embodiments, features, and aspects of the invention will be described in detail below with reference to the drawings.

Figure 1:
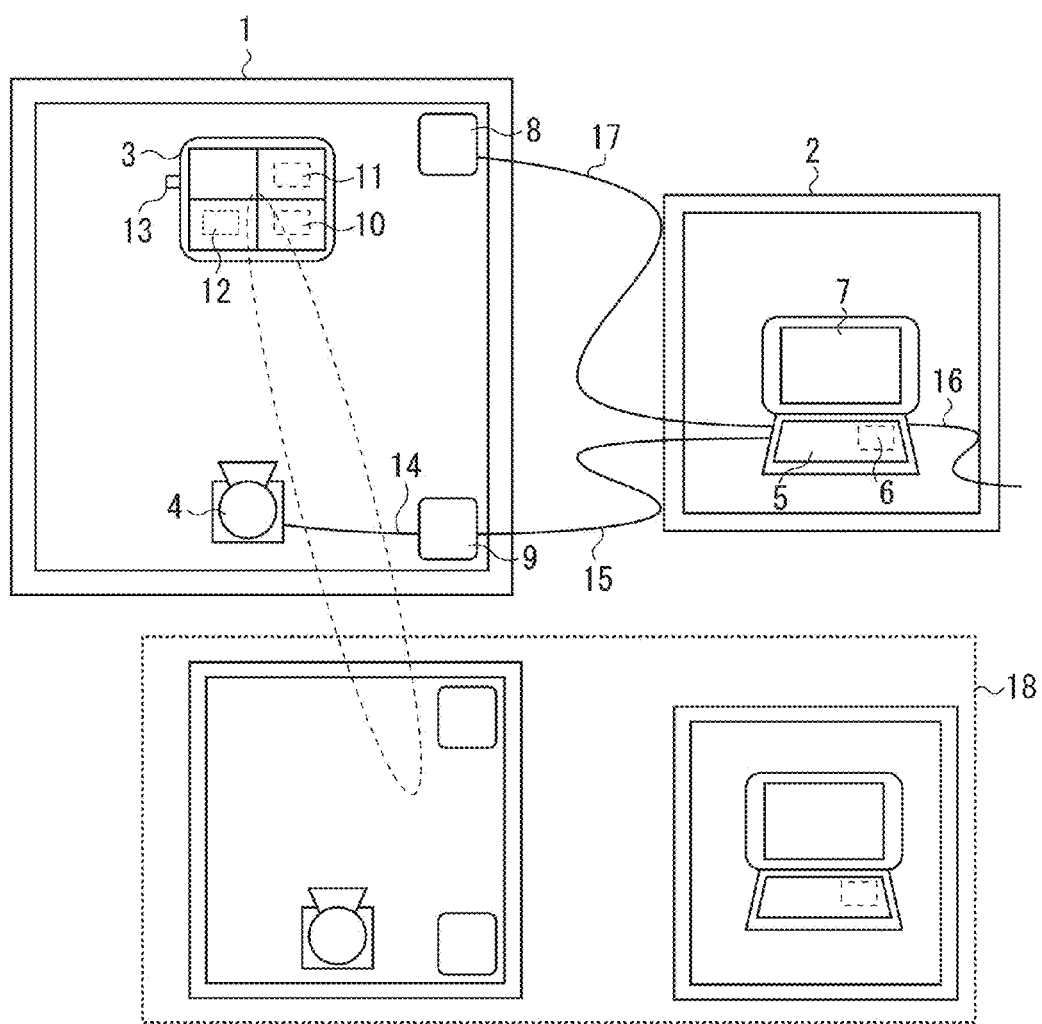
FIG. 1 illustrates a configuration of a radiation imaging system according to a first exemplary embodiment of the present invention.

FIG. 1 illustrates a configuration of a radiation imaging system according to a first exemplary embodiment of the present invention.

As illustrated in FIG. 1, a radiation imaging room 1 is a room for performing radiation imaging of an object by exposing it to radiation. A control room 2 is placed in the vicinity of the radiation imaging room 1. An electronic cassette (radiation imaging apparatus) 3 reacts with radiation and generates digital radiation image data. The electronic cassette 3 can be used while being moved among a plurality of radiation imaging rooms. The electronic cassette 3 includes a radiation detection unit that detects radiation and acquires a radiation image. Further, the electronic cassette 3 includes a storage unit that stores information concerning a plurality of radiation imaging control apparatuses.

A radiation generator 4 generates radiation. A radiation imaging control apparatus 5 controls communication, imaging conditions, an acquisition operation by the radiation detection unit, and the like. An image processing apparatus 6, such as a personal computer (PC), performs image processing. A display 7 is utilized to display digital radiation image data subjected to image processing, and a graphical user interface (GUI). An entry apparatus 8 is applicable to wireless communication such as Infrared Data Association (IrDA) communication. A synchronous access point 9 faces and wirelessly communicates with a wireless communication unit 10. The synchronous access point 9 also communicates with the radiation imaging control apparatus 5 and the image processing apparatus 6. The entry apparatus 8 and the synchronous access point 9 can be configured as either separate units or a single unit.

The wireless communication unit 10 performs wireless communication with the synchronous access point 9 using Institute of Electrical and Electronics Engineers (IEEE) 802.11 standards. A wireless communication unit 11 wirelessly communicates with the entry apparatus 8. A memory unit 12 stores parameter information to be transmitted when the wireless communication unit 10 wirelessly communicates with the entry apparatus 8 or the synchronous access point 9 provided in each radiation imaging room. The parameter information includes identification (ID) information representing a unique serial number of each radiation imaging apparatus, a physical channel (frequency or the like) for establishing wireless communication connection between the synchronous access point 9 and the wireless communication unit 10, a communication method (IEEE 802.11a, b, g, n, or the like), and an extended service set identifier (ESSID).

A transmission start input unit 13 is used to start communication of the wireless communication unit 10 and includes a radiation imaging control apparatus identification means. A connection cable 14 wiredly connects between the synchronous access point 9 and the radiation generator 4. A connection cable 15 wiredly connects between the synchronous access point 9 and the image processing apparatus 6. A backbone network 16 such as an in-hospital local area network (LAN) connects image processing apparatuses. A wired connection 17, such as a universal serial bus (USB), connects the entry apparatus 8 and the image processing apparatus 6. A set 18 of a second radiation imaging room and a control room has functions of the above described components 4 through 9 and 14 through 17.

Figure 2A:
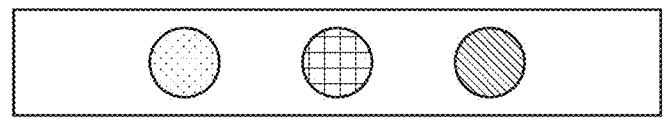
FIGS. 2A through 2E each illustrate a radiation imaging apparatus identification means in a transmission start input unit according to the first exemplary embodiment of the present invention.
Figure 2B:
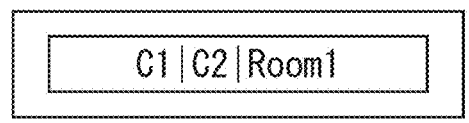

FIGS. 2A through 2E each illustrate a radiation imaging control apparatus identification means of the transmission start input unit 13. The radiation imaging control apparatus identification means illustrated in FIG. 2A is provided with buttons of the number equal to that of imaging apparatuses to be used. In FIG. 2B, the radiation imaging control apparatuses which can be connected for communication are displayed on a liquid crystal touch panel, and when a user touches a displayed location of a desired radiation imaging control apparatus, communication between the transmission start input unit 13 and the desired radiation imaging control apparatus 5 is started.

Figure 2C:
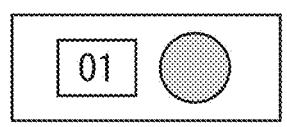
Figure 2D:
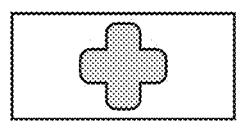
Figure 2E:
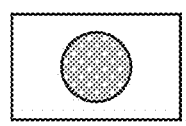

In FIG. 2C, a numerical value of a counter is associated with a type of the radiation imaging control apparatus and when the counter indicates an appropriate numerical value, a user pushes a button to start communication. FIG. 2D illustrates a directional switch in which a switching direction is associated with the type of the radiation imaging control apparatus 5 and a user pushes the button in an appropriate direction to start communication. FIG. 2E illustrates a color change button whose color is associated with the type of the radiation imaging control apparatus 5. Each time a user pushes the color change button, the color thereof changes. The user pushes the color change button relatively long when the button indicates an appropriate color, so that communication is started.

Figure 3B:
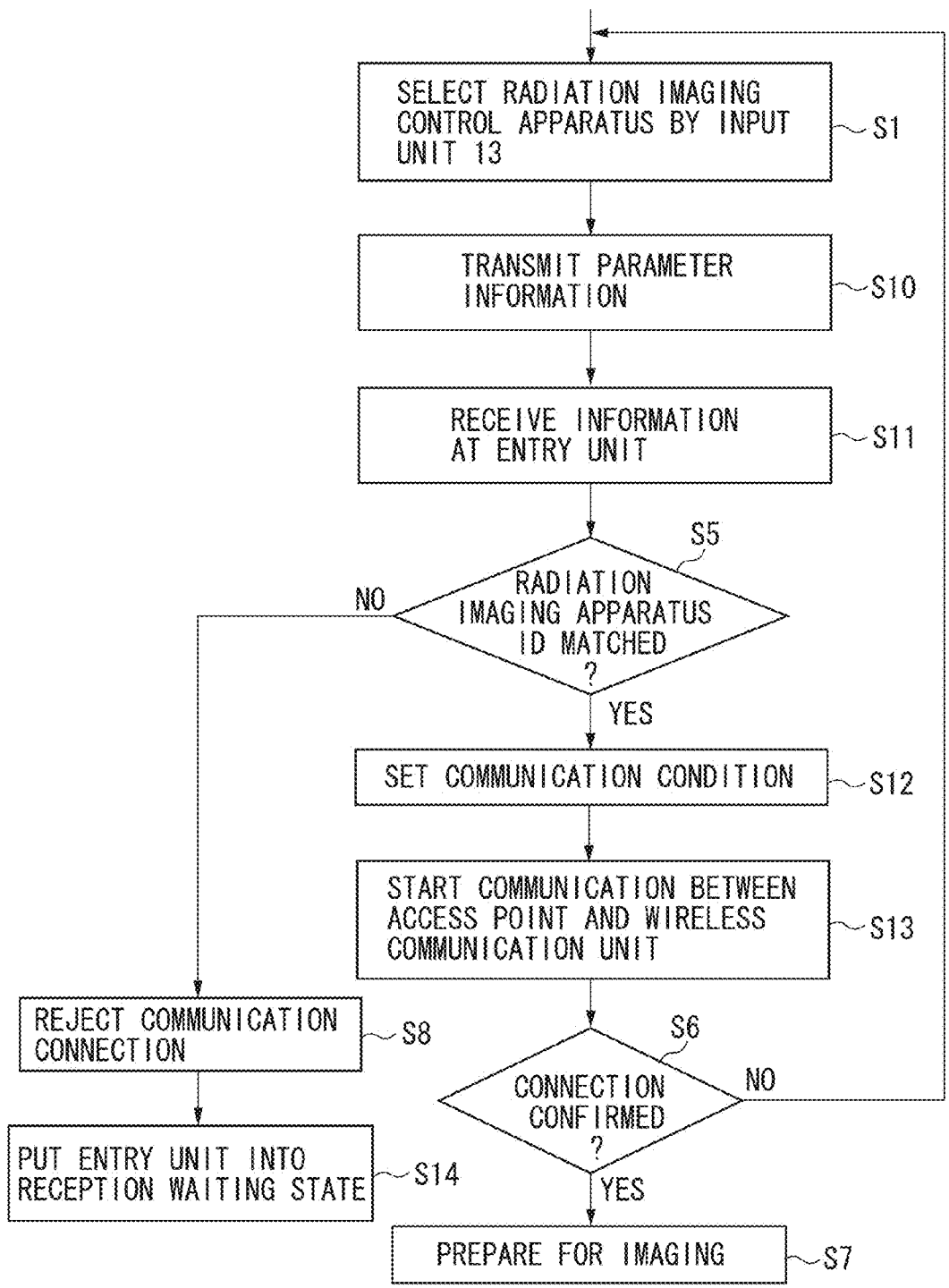

FIGS. 3A and 3B are flowcharts illustrating a process performed by the system according to the first exemplary embodiment of the present invention. FIG. 3A illustrates a case where a communication condition is changed at the electronic cassette. FIG. 3B illustrates a case where a communication condition is changed at the radiation imaging apparatus.

As illustrated in FIG. 3A, in step S1, a desired radiation imaging control apparatus 5 is selected by pushing down a transmission start input unit 13. In step S2, a communication condition for the wireless communication unit 10 is set on the electronic cassette side based on the parameter information corresponding to the desired radiation imaging control apparatus which is stored in the memory unit 12. In step S3, radiation imaging control apparatus ID information which is included in the parameter information stored in the memory unit 12 of the electronic cassette 3 is transmitted from the wireless communication unit 10. In step S4, the information transmitted in step S3 is received by the synchronous access point 9.

In step S5, the radiation imaging control apparatus 5 receives the information received in step S3 in the form of an interruption signal. Then, the radiation imaging control apparatus 5 determines whether a radiation imaging control apparatus with which the electronic cassette 3 wishes to communicate is the radiation imaging control apparatus 5 itself according to the radiation imaging control apparatus ID information. In step S6, the radiation imaging control apparatus 5 confirms that communication between the radiation imaging control apparatus 5 and the electronic cassette 3 is established.

In step S7, following the confirmation of the establishment of the wireless communication in the system, an operator starts preparation for imaging. On the other hand, in step S5, if the radiation imaging apparatus ID information does not match with the radiation imaging apparatus ID information on the received apparatus side (NO in step S5), the process proceeds to step S8 in which the radiation imaging control apparatus 5 issues a signal of rejecting communication connection.

In step S9, the synchronous access point 9 is put into a reception waiting state.

As illustrated in FIG. 3B, in step S10, information about a communication setting condition for establishing wireless communication connection between the synchronous access point 9 and the wireless communication unit 10, which is stored in the memory unit 12 of the electronic cassette 3, and the radiation imaging control apparatus ID information are transmitted from the wireless communication unit 11.

In step S11, the information transmitted in step S10 is received by the entry apparatus 8 which is always waiting for receiving the information. In step S12, a communication condition for the synchronous access point 9 is set according to the parameter information received in step S11. In step S13, communication between the synchronous access point 9 and the wireless communication unit 10 is started. In step S14, the entry apparatus 8 is put into a reception waiting state.

With the above described configuration, if the radiation imaging apparatus ID information matches with the radiation imaging apparatus ID information on the received apparatus side (YES in step S5), the process proceeds to step S6 or S12. If the radiation imaging apparatus ID information does not match with that of the received apparatus side (NO in step S5), the process proceeds to step S8. Then, if communication is not confirmed in step S6, the process returns to step S1, and the process in steps S1 through S6 is repeated again.

Each of the entry apparatus 8 and the synchronous access point 9 may have means for generating a sound and light and inform an operator in an imaging room of error information and necessity of reconnection when the process returns to step S1 or in step S8. According to the above described process illustrated in the flowchart, communication between the electronic cassette and the radiation imaging control apparatus can be started by the electronic cassette which an operator inevitably touches when imaging a radiation image. Accordingly, the present exemplary embodiment can provide a radiation imaging system with improved operability.

Figure 4:
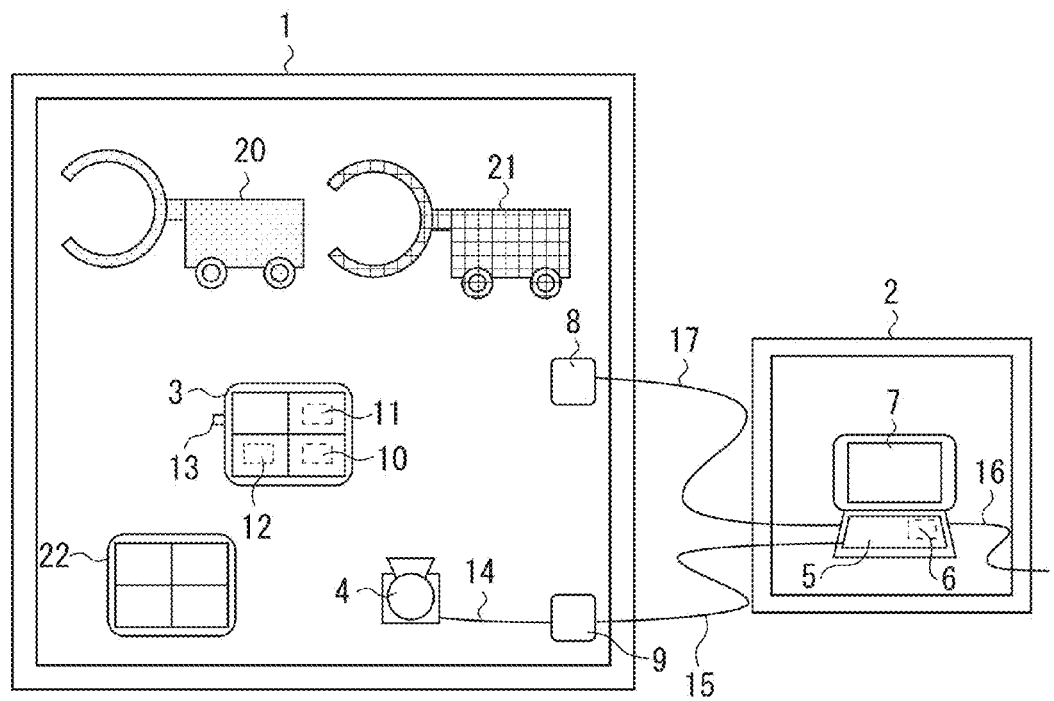
FIG. 4 illustrates a configuration of a radiation imaging system according to a second exemplary embodiment of the present invention.

FIG. 4 illustrates a configuration of a radiation imaging system according to a second exemplary embodiment of the present invention.

According to the second exemplary embodiment, not only when a single radiation imaging apparatus is provided in the imaging room, but also when a plurality of radiation imaging apparatuses are provided therein, an electronic cassette can designates a desired radiation imaging apparatus and communicate therewith. In addition, according to the second exemplary embodiment, when a plurality of electronic cassettes are provided, crossed line among the radiation imaging apparatuses and the electronic cassettes can be prevented.

Each of portable radiation imaging apparatuses 20 and 21 illustrated in FIG. 4 includes the components 4 through 9 and 14 through 17 according to the first exemplary embodiment. An electronic cassette 22 wirelessly communicable with a radiation imaging control apparatus 5 and the like includes the components 10 through 13 according to the first exemplary embodiment. The memory unit 12 stores the parameter information such as ID information of each radiation imaging apparatus, a physical channel for establishing wireless communication connection between the synchronous access point and the wireless communication unit 10, a communication method, and an ESSID. The transmission start input unit 13 can identify a radiation imaging apparatus according to a direction of a tube or a position information of the radiation generator, instead of the type of the radiation imaging apparatus described in the first exemplary embodiment.

Figure 5:
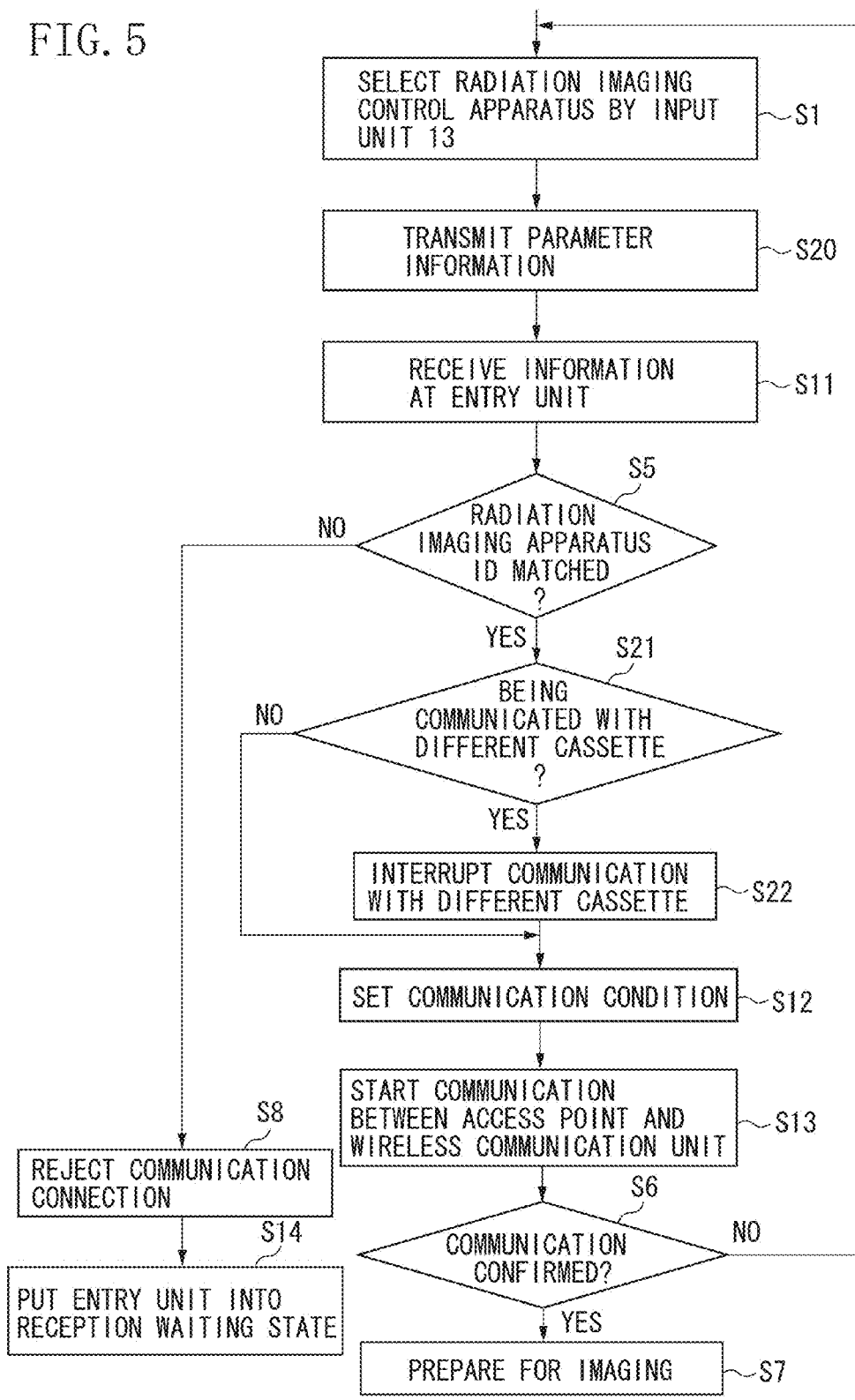
FIG. 5 is a flowchart illustrating a process performed by the system according to the second exemplary embodiment of the present invention.

FIG. 5 is a flowchart illustrating a process performed by the system according to the second exemplary embodiment.

As illustrated in FIG. 5, in step S20, ID information about a desired radiation imaging apparatus stored in the memory 12 of the electronic cassette 3 and the parameter information for establishing wireless communication connection between the synchronous access point of the desired radiation imaging apparatus and the wireless communication unit 10 are transmitted. In step S21, it is determined whether a desired radiation imaging control apparatus is communicating with a different electronic cassette according to the communication setting condition represented by the parameter information received in step S11 differs from a current communication setting condition. In step S22, communication with the different electronic cassette whose communication setting condition is different from the current communication setting condition is interrupted.

With the above described configuration, if it is determined that the current communication setting condition differs from the communication setting condition received in step S11 (YES in step S21), the process proceeds to step S22 in which the communication connection to the electronic cassette currently communicated therewith is interrupted. On the other hand, if it is determined that the current communication setting condition is the same as the communication setting condition received in step S11 (NO in step S21), the process proceeds to step S12 by skipping step S22. Then, the system advances to an imaging operation.

If processing in step S22 is not performed, processing in step S6 can be omitted.

According to the above described process illustrated in the flowchart, the electronic cassette can designate a radiation imaging control apparatus for performing desired wireless communication among a plurality of radiation imaging control apparatuses and communicate therewith. Even if there is a plurality of electronic cassettes, the system can establish communication between the desired electronic cassette and the desired radiation imaging control apparatus even when another electronic cassette is in a state which can communicate with the desired radiation imaging control apparatus. Consequently, a wrong electronic cassette can be prevented from being used to the communication. Accordingly, operability can be enhanced.

Figure 6:
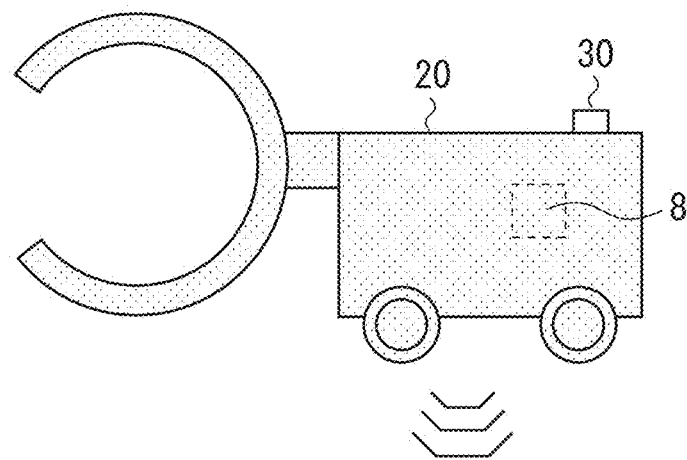
FIG. 6 illustrates a configuration of a radiation imaging system according to a third exemplary embodiment of the present invention.
Figure 6:
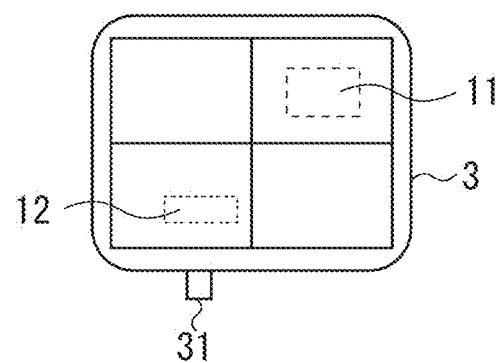

FIG. 6 illustrates a configuration of a radiation imaging system according to a third exemplary embodiment of the present invention.

The present exemplary embodiment takes into consideration a method for registering parameter information, such as radiation imaging apparatus ID information and a communication setting condition, in a memory unit of an electronic cassette.

As illustrated in FIG. 6, a registration start input means 30 of a radiation imaging apparatus 20 is used to start transmission of the parameter information. A registration/reception start input means 31 is used to start reception and registration of the parameter information in the memory unit 12 of the electronic cassette 3. The registration/reception start input means 31 and the transmission start input unit 13 can be configured as a single unit. It is desirable that an entry apparatus 8 of the radiation imaging apparatus side and a wireless communication unit 11 of the electronic cassette side, which are applicable to wireless communication such as IrDA communication to be performed at relatively close range, are used for registration of the parameter information in the electronic cassette.

Figure 7:
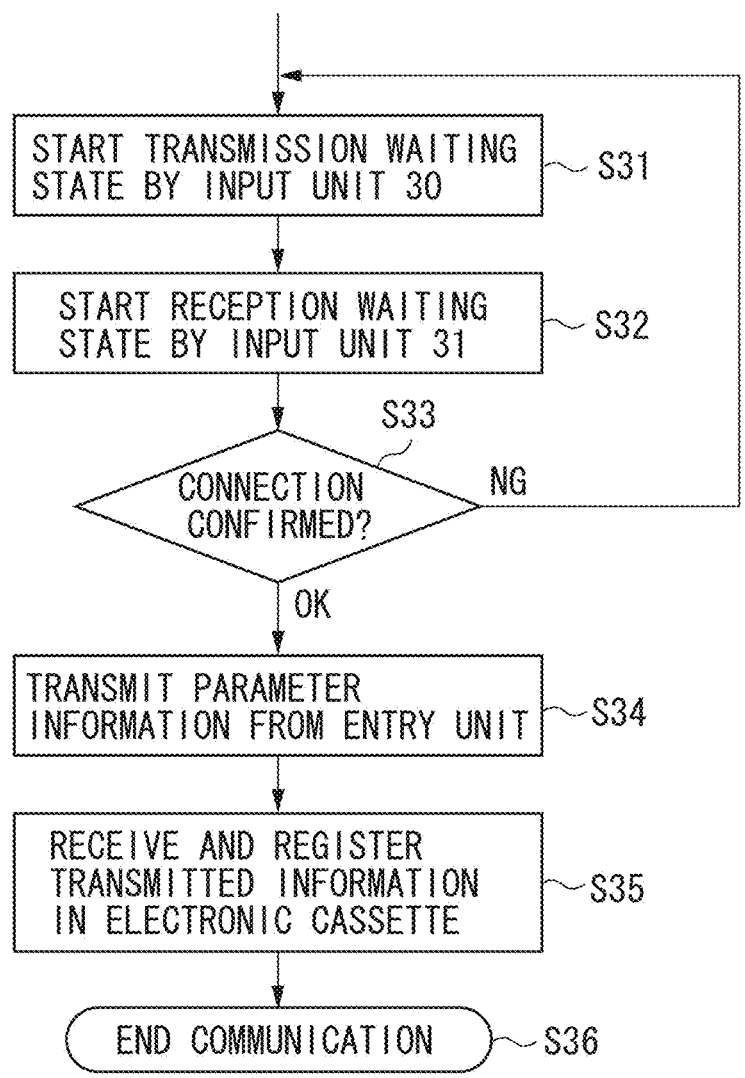
FIG. 7 is a flowchart illustrating a process performed by the system according to the third exemplary embodiment of the present invention.

FIG. 7 is a flowchart illustrating an operation of the system according to the third exemplary embodiment of the present invention.

As illustrated in FIG. 7, in step S31, a transmission waiting state is started by pushing down the registration start input means 30. In step S32, a reception waiting state is started by pushing down the registration/reception start input means 31. Either of processing in step S31 and that in step S32 can be performed first. In step S33, each of the radiation imaging apparatus and the electronic cassette confirms whether communication connection therebetween is established. In step S34, the parameter information including the radiation imaging apparatus ID information and the communication setting condition is transmitted from the entry apparatus 8. In step S35, the wireless communication unit 11 receives the information transmitted in step S34 and registers the received information in the memory unit 12. In step S36, the communication connection is terminated and interrupted.

With the above described configuration, the parameter information is transmitted from the radiation imaging control apparatus by pushing down the registration start input means 30. Before or after the transmission of the parameter information, the registration/reception start input means 31 is used, so that the electronic cassette can receive a signal from the radiation imaging control apparatus and register the parameter information in the memory unit 12.

In addition, information about the radiation imaging apparatus usable in the backbone network 16 such as the in-hospital LAN described in the first exemplary embodiment may be collectively managed. Thus, the parameter information corresponding to a plurality of radiation imaging control apparatuses can be registered at one time. Consequently, if an available radiation imaging control apparatus is newly increased, parameter information about the new radiation imaging control can be registered immediately, so that the electronic cassette can communicate with a desired radiation imaging control apparatus. Accordingly, a radiation imaging system whose operability is more improved can be provided.

In the foregoing description, mainly exemplary embodiments relating to the wireless communication between the radiation imaging apparatus (electronic cassette) and the radiation imaging control apparatus have been described. However, the exemplary embodiments of the present invention are not limited to the wireless communication. The exemplary embodiments of the present invention can be applied to a radiation imaging system in which a plurality of radiation imaging control apparatuses coexist by being wiredly connected.

Aspects of the present invention can also be realized by a computer of a system or apparatus (or devices such as a CPU or MPU) that reads out and executes a program recorded on a memory device to perform the functions of the above-described embodiment (s), and by a method, the steps of which are performed by a computer of a system or apparatus by, for example, reading out and executing a program recorded on a memory device to perform the functions of the above-described embodiment (s). For this purpose, the program is provided to the computer for example via a network or from a recording medium of various types serving as the memory device (e.g., computer-readable medium).

While the present invention has been described with reference to exemplary embodiments, it is to be understood that the invention is not limited to the disclosed exemplary embodiments. The scope of the following claims is to be accorded the broadest interpretation so as to encompass all modifications, equivalent structures, and functions.

This application claims priority from Japanese Patent Application No. 2009-288829 filed Dec. 21, 2009, which is hereby incorporated by reference herein in its entirety.

What is claimed is:

1. A radiation imaging apparatus communicating with a radiation imaging control apparatus for controlling an operation of acquiring a radiation image, the radiation imaging apparatus comprising:
   a radiation detection unit arranged in a case and configured to detect radiation and to acquire the radiation image;
   a storage unit configured to store information about a plurality of the radiation imaging control apparatuses;
   a selection unit configured to select at least one of the plurality of the radiation imaging control apparatuses as an apparatus to communicate with the radiation imaging apparatus, the selection unit being arranged on the case in which the radiation detection unit is arranged; and
   a setting unit configured to set communication with the radiation imaging control apparatus selected by the selection unit.

2. The radiation imaging apparatus according to claim 1, wherein communication between the radiation imaging control apparatus and the radiation imaging apparatus is wireless communication.

3. The radiation imaging apparatus according to claim 1, further comprising a change unit configured to change communication with the radiation imaging control apparatus selected by the selection unit to that with a radiation imaging control apparatus different from the radiation imaging control apparatus selected by the selection unit.

4. The radiation imaging apparatus according to claim 1, further comprising a display unit configured to display the information about the plurality of the radiation imaging control apparatuses which is stored in the storage unit.

5. The radiation imaging apparatus according to claim 1, further comprising a display unit configured to display information about the radiation imaging control apparatus with which wireless communication is set.

6. The radiation imaging apparatus according to claim 1, further comprising a registration unit configured to register information about the plurality of the radiation imaging control apparatuses in the storage unit.

7. The radiation imaging apparatus according to claim 1, wherein the selection unit includes buttons of a number equal to that of imaging apparatuses to be used.

8. The radiation imaging apparatus according to claim 1, wherein the selection unit includes a touch panel for selecting the radiation imaging control apparatus.

9. The radiation imaging apparatus according to claim 1, wherein the selection unit includes a touch panel for displaying the radiation imaging control apparatuses which can be connected for communication.

10. The radiation imaging apparatus according to claim 1, wherein the selection unit includes a counter associated with a type of the radiation imaging control apparatus.

11. The radiation imaging apparatus according to claim 1, wherein the selection unit includes a color change button whose color is associated with the type of the radiation imaging control apparatus.

12. A radiation imaging system including comprising a radiation imaging control apparatus configured to control an operation of acquiring a radiation image and a radiation imaging apparatus configured to communicate with the radiation imaging control apparatus,
   wherein the radiation imaging apparatus comprises:
   a radiation detection unit arranged in a case and configured to detect radiation and to acquire the radiation image;
   a storage unit configured to store information about a plurality of the radiation imaging control apparatuses;
   a selection unit configured to select at least one of the plurality of the radiation imaging control apparatuses as an apparatus to communicate with the radiation imaging apparatus, the selection unit being arranged on the case in which the radiation detection unit is arranged; and
   a setting unit configured to set communication with the radiation imaging control apparatus selected by the selection unit.

13. A radiation imaging apparatus communicating with a radiation imaging control apparatus for controlling an operation of acquiring a radiation image, the radiation imaging apparatus comprising:
   a radiation detection unit configured to detect radiation and to acquire the radiation image;
   a storage unit configured to store information about a plurality of the radiation imaging control apparatuses;
   a selection unit configured to select at least one of the plurality of the radiation imaging control apparatuses as an apparatus to communicate with the radiation imaging apparatus, the selection unit being arranged on the surface of the radiation imaging apparatus; and
   a setting unit configured to set communication with the radiation imaging control apparatus selected by the selection unit.

14. The radiation imaging apparatus according to claim 13, wherein the selection unit includes buttons of a number equal to that of imaging apparatuses to be used.

15. The radiation imaging apparatus according to claim 13, wherein the selection unit includes a touch panel for selecting the radiation imaging control apparatus.

16. The radiation imaging apparatus according to claim 13, wherein the selection unit includes a touch panel for displaying the radiation imaging control apparatuses which can be connected for communication.

17. The radiation imaging apparatus according to claim 13, wherein the selection unit includes a counter associated with a type of the radiation imaging control apparatus.

18. The radiation imaging apparatus according to claim 13, wherein the selection unit includes a color change button whose color is associated with the type of the radiation imaging control apparatus.

* * * * *